United States Patent
Gong et al.

(10) Patent No.: US 10,604,474 B2
(45) Date of Patent: Mar. 31, 2020

(54) CRYSTALLINE FORM OF GAMMA-AMINOBUTYRIC ACID AND PREPARATION METHOD THEREOF

(71) Applicants: NANTONG LICHENG BIOLOGICAL ENGINEERING CO., LTD, Nantong, Jiangsu (CN); TIANJIN UNIVERSITY, Tianjin (CN)

(72) Inventors: Junbo Gong, Tianjin (CN); Kaifei Zhao, Tianjin (CN); Haiyan Xi, Jiangsu (CN); Xiaohua Wu, Jiangsu (CN); Baohong Hou, Tianjin (CN); Qiuxiang Yin, Tianjin (CN); Jingkang Wang, Tianjin (CN); Feng Jin, Jiangsu (CN); Shichao Du, Tianjin (CN); Qinqing Gu, Jiangsu (CN); Shiping Tang, Jiangsu (CN)

(73) Assignees: Nantong Licheng Biological Engineering Co., Ltd, Nantong (CN); Tianjin University, Tianjin (CN)

( * ) Notice: Subject to any disclaimer, the term of this patent is extended or adjusted under 35 U.S.C. 154(b) by 0 days.

(21) Appl. No.: 16/078,008

(22) PCT Filed: Nov. 7, 2016

(86) PCT No.: PCT/CN2016/104905
§ 371 (c)(1),
(2) Date: Aug. 15, 2018

(87) PCT Pub. No.: WO2018/082096
PCT Pub. Date: May 11, 2018

(65) Prior Publication Data
US 2019/0225574 A1 Jul. 25, 2019

(51) Int. Cl.
*C07C 229/08* (2006.01)
*C07C 227/40* (2006.01)

(52) U.S. Cl.
CPC .......... *C07C 229/08* (2013.01); *C07C 227/40* (2013.01); *C07B 2200/13* (2013.01)

(58) Field of Classification Search
CPC .. C07C 227/40; C07C 229/08; C07B 2200/13
See application file for complete search history.

(56) References Cited

FOREIGN PATENT DOCUMENTS

| CN | 100999479 A | 7/2007 |
|----|-------------|--------|
| CN | 101928736 A | 12/2010 |
| CN | 102242161 A | 11/2011 |
| CN | 103130664 A | 6/2013 |
| CN | 103509831 A | 1/2014 |
| CN | 104531795 A | 4/2015 |
| CN | 105838747 A | 8/2016 |

OTHER PUBLICATIONS

Tomita et al., Crystal and Molecular Structure of ω-Amino Acids, ω-Amino Sulfonic Acids and Their Derivatives. IV. The Crystal and Molecular Structure of γ-Aminobutyric Acid (GABA), a Nervous Inhibitory Transmitter, Bulletin of the Chemical Society of Japan, vol. 46, Issue 7, pp. 2199-2204 (Year: 1973).*
International Search Report of PCT Patent Application No. PCT/CN2016/104905 dated Jul. 24, 2017.
Ma, Qiang, Study on the Crystallization Process of Gamma-amino Butyric Acid, Science-Engineering (A), China Master's Theses Full-Text Database, Dec. 15, 2011, Figure 2-2.

* cited by examiner

*Primary Examiner* — Paul A Zucker

(57) ABSTRACT

A method for preparing a new crystalline form of γ-aminobutyric acid, including the steps of: S1: preparing a γ-aminobutyric acid solution at an initial concentration of 0.5-1.0 g/mL by adding crude γ-aminobutyric acid to water; adding an additive to the γ-aminobutyric acid solution, raising the temperature to 50-80° C., stirring to produce a clear solution; and S2: obtaining a suspension by evaporating water from the product of S1 under reduced pressure and at 50-80° C.; obtaining a wet product by filtering the suspension; drying the wet product to obtain the new crystalline form of γ-aminobutyric acid. The preparation method of the new crystalline form of γ-aminobutyric acid is simple, easy to operate, low in energy consumption, economical and environmentally friendly. It is suitable for large-scale industrial production.

6 Claims, 3 Drawing Sheets

CRYSTALLINE FORM OF GAMMA-AMINOBUTYRIC ACID AND PREPARATION METHOD THEREOF

FIELD OF THE INVENTION

The invention relates to the technical field of drug crystallization, in particular to a new crystalline form of γ-aminobutyric acid and preparation method thereof.

BACKGROUND OF THE INVENTION

γ-aminobutyric acid (GABA), chemical name 4-aminobutyric acid, is also known as aminobutyric acid or piperidinic acid. Its molecular formula is $C_4H_9NO_2$, and its molecular mass is 103.1. It appears as a white or off-white crystalline powder. It is a hydrophilic amino acid, and its structural formula is as follows:

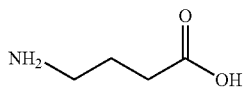

In mammals, γ-aminobutyric acid is an inhibitory neurotransmitter that mediates more than 40% of inhibitory nerve signals. It has important physiological functions and broad application prospects in pharmaceutical production. In addition, in the food industry, γ-aminobutyric acid can be used in the production of food additives and the development of functional dairy products and bakery products. It can also be employed in sports food and the beverage industry. The Ministry of Health of the People's Republic of China has approved γ-aminobutyric acid as a new resource food.

At present, the research on γ-aminobutyric acid has attracted much attention at home and abroad. Various methods have been employed to prepare different crystalline forms of γ-aminobutyric acid. For example, patents CN101928736A, CN103509831A, CN104531795A have disclosed the preparation of γ-aminobutyric acid via evaporative concentration of a γ-aminobutyric acid fermentation broth, 95% ethanol is then added to the concentrated liquid, followed by stirring, precipitating and crystallization. The product has a crystal morphology that is either needle-shaped or sheet-shaped; it has a dim color and low purity; its main particle size is small, and its particle size is unevenly distributed; it has low bulk density and low flowability, which is not suitable for further processing and use. Patent CN102242161A has disclosed the preparation of γ-aminobutyric acid by a three-effect concentration and direct condensation-crystallization method. The specific steps are: the fermentation broth is evaporated to a certain degree under three different temperature conditions, and then transferred into a vacuum concentration crystallizer, concentrated to obtain the crystals; finally, the crystals are naturally cooled at atmospheric pressure for 1 to 1.5 hours to obtain γ-aminobutyric acid. The crystal morphology of the product is powder-shaped. When exposed to air, the product easily absorbs water and agglomerates into clumps, causing inconveniences in further processing and use. Furthermore, the above preparation procedures are complicated; the preparation method is high in cost and energy consumption, and low in yield, it is not suitable for large-scale industrial production. The chemical reagents used may pose harm to human body and the environment.

Therefore, it is necessary to provide a new crystalline form of γ-aminobutyric acid which is stable, can easily be absorbed and used, does not easily absorb moisture and agglomerate, has large main particle size, uniform particle size distribution, high bulk density and good flowability. It is also necessary to provide a corresponding preparation method which is easy to perform, low in energy consumption, economical, environmentally friendly, and suitable for large-scale industrial production.

SUMMARY OF THE INVENTION

The objective of the present invention is to overcome the shortcomings of the prior art and to provide a new crystalline form of γ-aminobutyric acid and preparation method thereof.

The technical solution of the present invention is:

A new crystalline form of γ-aminobutyric acid, the X-ray powder diffraction pattern of the new crystalline form has characteristic absorption peaks at diffraction angles 2θ of 14.8°±0.2°, 15.7°±0.2°, 17.6°±0.2°, 18.9°±0.2°, 21.0°±0.2°, 23.5°±0.2°, 27.5°±0.2°, 29.9°±0.2°, 31.4°±0.2°, 32.2°±0.2°, 33.3°±0.2°, 33.8°±0.2°, 35.6°±0.2°, 38.3°±0.2°.

Furthermore, the new crystalline form exhibits an endothermic characteristic peak at (220±2) °C. in DSC (Differential Scanning calorimetry) analysis.

The present invention also discloses a method for preparing a new crystalline form of γ-aminobutyric acid, including the steps of:

S1: preparing a γ-aminobutyric acid solution at an initial concentration of 0.5-1.0 g/mL by adding crude γ-aminobutyric acid to water; adding an additive to the γ-aminobutyric acid solution, raising the temperature to 50-80° C., stirring to produce a clear solution; and S2: obtaining a suspension by evaporating water from the product of S1 under reduced pressure and at 50-80° C.; obtaining a wet product by filtering the suspension; drying the wet product to obtain the new crystalline form of γ-aminobutyric acid.

Preferably, the additive in step S1 is one or more selected from sodium acetate, potassium acetate, and ammonium acetate; the mass ratio of the additive to the crude γ-aminobutyric acid is 0.1:100-0.5:100.

Preferably, evaporating water under reduced pressure in step S2 is performed under a vacuum of 0.06-0.09 MPa.

Preferably, in step S2, the volumetric ratio of water evaporated under reduced pressure to water present initially is 30:100 to 80:100, and evaporation time is 0.5 to 4 hours.

Preferably, the drying in step S2 refers to drying at a temperature of 30-60° C. and under atmospheric pressure for 8-12 hours.

Different from preparation methods of the prior art, the preparation method provided by the present invention is to obtain a new crystalline form of γ-aminobutyric acid by evaporating solvent in the presence of a certain amount of additive. Its mechanism is that under the action of an additive molecule, the accumulation process of γ-aminobutyric acid molecules is changed; crystal nucleation can thereby be controlled.

Comparing with the prior art, the beneficial effects of the new crystalline form of γ-aminobutyric acid and preparation method thereof of the present invention are as follows:

(1) The new crystalline form of γ-aminobutyric acid of the present invention is not susceptible to absorbing moisture and agglomeration, and is convenient for further processing and use.

(2) The new crystalline form of γ-aminobutyric acid of the present invention has large main particle size, uniform particle size distribution, high bulk density, good flowability, and can be easily absorbed and used.

(3) The preparation method of the new crystalline form of γ-aminobutyric acid according to the present invention is simple, easy to operate, low in energy consumption, economical and environmentally friendly. It is suitable for large-scale industrial production.

BRIEF DESCRIPTION OF THE DRAWINGS

To more clearly illustrate the technical solutions of the present invention, the accompanying drawings mentioned in the embodiments or prior art will be briefly described. It is obvious that the drawings described hereafter are merely embodiments of the present invention. For a person of ordinary skill in the art, other drawings may also be obtained based on these drawings without any creative effort.

DETAILED DESCRIPTION OF THE ILLUSTRATED EMBODIMENTS

The technical solutions in the embodiments of the present invention will be described clearly and completely hereafter with reference to the accompanying drawings. Obviously, the described embodiments are merely some, but not all, of the embodiments of the present invention. Any other embodiments obtained by a person having ordinary skill in the art based on the embodiments of the present invention without creative efforts shall fall within the protection scope of the present invention.

Embodiment 1

The present invention discloses a method for preparing a new crystalline form of γ-aminobutyric acid, including the steps of:

S1: 50 g crude γ-aminobutyric acid was added to 100 mL water to prepare a γ-aminobutyric acid solution with an initial concentration of 0.5 g/mL; 0.05 g sodium acetate was added to the solution, and the temperature was elevated to 50° C.; the mixture was stirred to give a clear solution.

S2: The product of S1 was evaporated under reduced pressure at a temperature of 50° C. and a vacuum of 0.09 MPa for 4 hours; 80 mL water was evaporated out, and a suspension was obtained. The suspension was filtered to obtain a wet product, the wet product was dried at 60° C. and atmospheric pressure for 8 hours until its weight was constant. A new crystalline form of γ-aminobutyric acid was obtained as the product.

The purity of the new crystalline form of γ-aminobutyric acid of the present embodiment was 99.5% as determined by high-performance liquid chromatography (HPLC).

Figure 1:
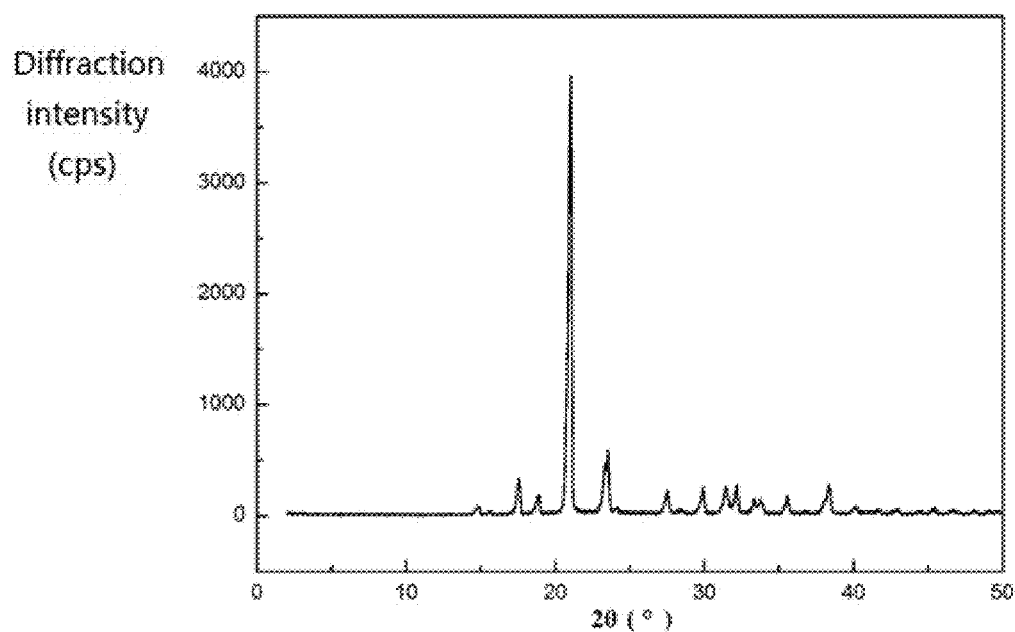
FIG. 1 is an X-ray powder diffraction pattern of a new crystalline form of γ-aminobutyric acid obtained in embodiment 1 of the present invention.

An XRD test of the new crystalline form of γ-aminobutyric acid of the present embodiment was performed using a D/max-rA X-ray diffractometer from Rigaku Cooperation (Japan). As shown in FIG. 1, the X-ray powder diffraction pattern of the product had characteristic absorption peaks at diffraction angles 2θ of 14.83°, 15.67°, 17.61°, 18.94°, 21.02°, 23.48°, 27.52°, 29.90°, 31.37°, 32.18°, 33.31°, 33.82°, 35.62° and 38.30°.

Figure 2:
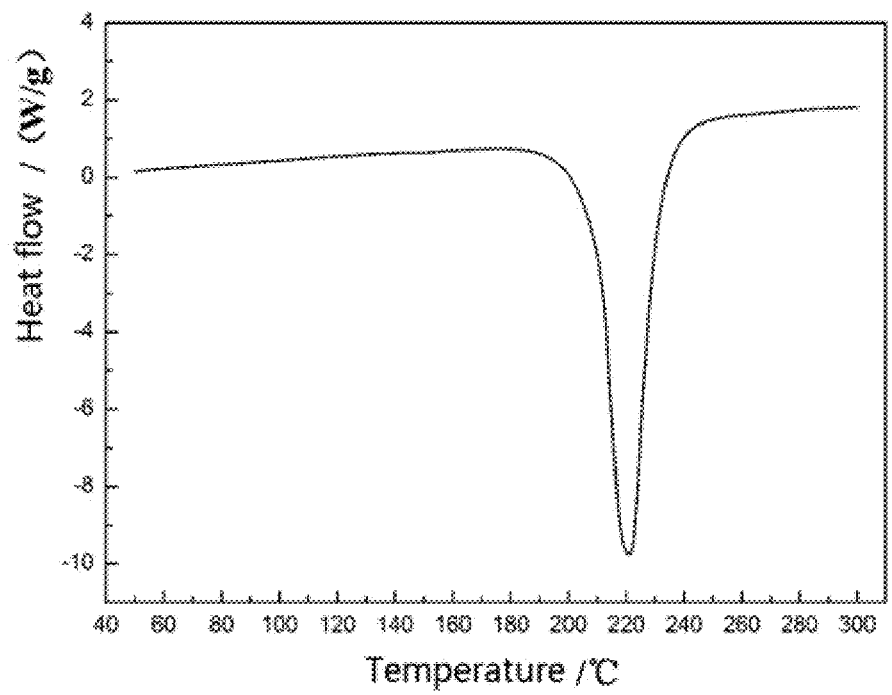
FIG. 2 is a DSC diagram of the new crystalline form of γ-aminobutyric acid obtained in embodiment 1 of the present invention.

DSC (Differential Scanning calorimetry) analysis was used to examine the new crystalline form of γ-aminobutyric acid of the present embodiment. As shown in FIG. 2, the product exhibited an endothermic characteristic peak at 220° C.

Figure 3:
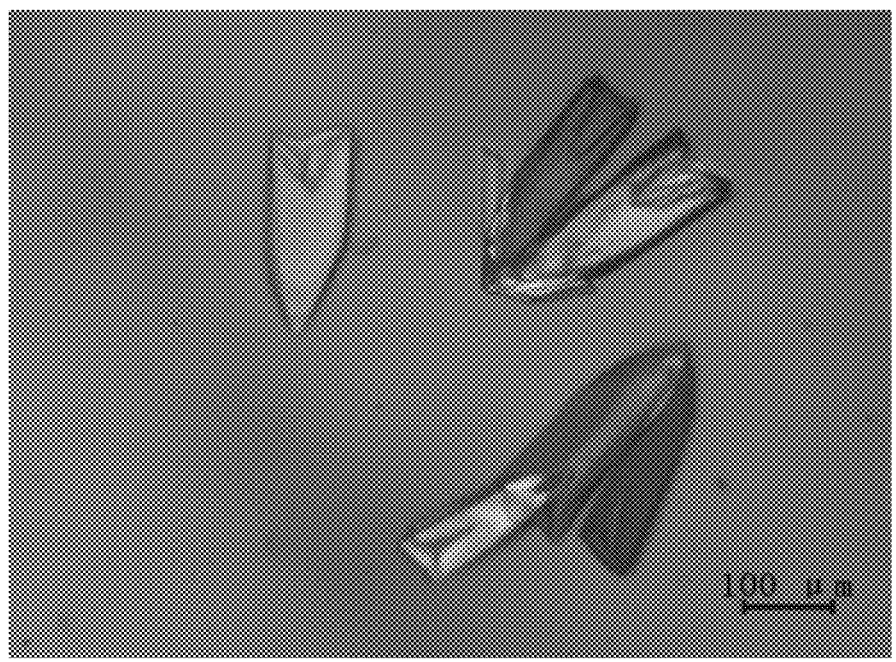
FIG. 3 is an SEM image of the new crystalline form of γ-aminobutyric acid obtained in embodiment 1 of the present invention.

The new crystalline form of γ-aminobutyric acid of the present embodiment was characterized by Scanning Electron Microscopy (SEM). As shown in FIG. 3, the product appeared conical-block-shaped. Its main particle size was 150 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 35°, indicating that the product had good flowability.

The bulk density of the new crystalline form of γ-aminobutyric acid of the present embodiment was 0.8 g/mL. This shows that the product had high bulk density.

Embodiment 2

The present invention discloses a method for preparing a new crystalline form of γ-aminobutyric acid, including the steps of:

S1: 100 g crude γ-aminobutyric acid was added to 100 mL water to prepare a γ-aminobutyric acid solution with an initial concentration of 1 g/mL; 0.5 g potassium acetate was added to the solution, and the temperature was elevated to 80° C.; the mixture was stirred to give a clear solution.

S2: The product of S1 was evaporated under reduced pressure at a temperature of 80° C. and a vacuum of 0.06 MPa for 0.5 hours; 30 mL water was evaporated out, and a suspension was obtained. The suspension was filtered to obtain a wet product, the wet product was dried at 30° C. and atmospheric pressure for 12 hours until its weight was constant. A new crystalline form of γ-aminobutyric acid was obtained as the product.

The purity of the new crystalline form of γ-aminobutyric acid of the present embodiment was 99.7% as determined by high-performance liquid chromatography (HPLC).

An XRD test of the new crystalline form of γ-aminobutyric acid of the present embodiment was performed using a D/max-rA X-ray diffractometer from Rigaku Cooperation (Japan). The results showed that the X-ray powder diffraction pattern of the product had characteristic absorption peaks at diffraction angles 2θ of 14.90°, 15.82°, 17.51°, 18.94°, 21.13°, 23.43°, 27.54°, 29.90°, 31.31°, 32.12°, 33.13°, 33.92°, 35.58° and 38.37°.

DSC (Differential Scanning calorimetry) analysis was used to examine the new crystalline form of γ-aminobutyric acid of the present embodiment. The results showed that the product exhibited an endothermic characteristic peak at 218° C.

The new crystalline form of γ-aminobutyric acid of the present embodiment was characterized by Scanning Electron Microscopy (SEM). SEM images showed that the product appeared conical-block-shaped. Its main particle size was 170 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 37°, indicating that the product had good flowability.

The bulk density of the new crystalline form of γ-aminobutyric acid was 0.7 g/mL. This shows that the product had high bulk density.

Embodiment 3

The present invention discloses a method for preparing a new crystalline form of γ-aminobutyric acid, including the steps of:

S1: 75 g crude γ-aminobutyric acid was added to 100 mL water to prepare a γ-aminobutyric acid solution with an initial concentration of 0.75 g/mL; 0.2 ammonium acetate was added to the solution, and the temperature was elevated to 60° C.; the mixture was stirred to give a clear solution.

S2: The product of S1 was evaporated under reduced pressure at a temperature of 60° C. and a vacuum of 0.08 MPa for 3 hours; 50 mL water was evaporated out, and a suspension was obtained. The suspension was filtered to obtain a wet product, the wet product was dried at 50° C. and atmospheric pressure for 9 hours until its weight was constant. A new crystalline form of γ-aminobutyric acid was obtained as the product.

The purity of the new crystalline form of γ-aminobutyric acid of the present embodiment was 99.1% as determined by high-performance liquid chromatography (HPLC).

An XRD test of the new crystalline form of γ-aminobutyric acid of the present embodiment was performed using a D/max-rA X-ray diffractometer from Rigaku Cooperation (Japan). The results showed that the X-ray powder diffraction pattern of the product had characteristic absorption peaks at diffraction angles 2θ of 14.78°, 15.62°, 17.40°, 18.90°, 21.20°, 23.33°, 27.48°, 29.71°, 31.42°, 32.21°, 33.12°, 34.0°, 35.61°, and 38.13°.

DSC (Differential Scanning calorimetry) analysis was used to test the new crystalline form of γ-aminobutyric acid of the present embodiment. The results showed that the product exhibited an endothermic characteristic peak at 221° C.

The new crystalline form of γ-aminobutyric acid of the present embodiment was characterized by Scanning Electron Microscopy (SEM). SEM images showed that the product appeared conical-block-shaped. Its main particle size was 140 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 34°, indicating that the product had good flowability.

The bulk density of the new crystalline form of γ-aminobutyric acid was 0.85 g/mL. This shows that the product had high bulk density.

Embodiment 4

The present invention discloses a method for preparing a new crystalline form of γ-aminobutyric acid, including the steps of:

S1: 80 g crude γ-aminobutyric acid was added to 100 mL water to prepare a γ-aminobutyric acid solution with an initial concentration of 0.8 g/mL; 0.1 g sodium acetate and 0.2 g ammonium acetate were added to the solution, and the temperature was elevated to 70° C.; the mixture was stirred to give a clear solution.

S2: The product of S1 was evaporated under reduced pressure at a temperature of 70° C. and a vacuum of 0.07 MPa for 1 hour; 60 mL water was evaporated out, and a suspension was obtained. The suspension was filtered to obtain a wet product, the wet product was dried at 40° C. and atmospheric pressure for 10 hours until its weight was constant. A new crystalline form of γ-aminobutyric acid was obtained as the product.

The purity of the new crystalline form of γ-aminobutyric acid of the present embodiment was 99.0% as determined by high-performance liquid chromatography (HPLC).

An XRD test of the new crystalline form of γ-aminobutyric acid was performed using a D/max-rA X-ray diffractometer from Rigaku Cooperation (Japan). The results showed that the X-ray powder diffraction pattern of the product had characteristic absorption peaks at diffraction angles 2θ of 15.0°, 15.50°, 17.80°, 18.94°, 21.02°, 23.39°, 27.58°, 29.87°, 31.22°, 32.31°, 33.33°, 33.92°, 35.46°, and 38.42°.

DSC (Differential Scanning calorimetry) analysis was used to test the new crystalline form of γ-aminobutyric acid of the present embodiment. The results showed that the product exhibited an endothermic characteristic peak at 219° C.

The new crystalline form of γ-aminobutyric acid of the present embodiment was characterized by Scanning Electron Microscopy (SEM). SEM images showed that the product appeared conical-block-shaped. Its main particle size was 165 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 36°, indicating that the product had good flowability.

The bulk density of the new crystalline form of γ-aminobutyric acid was 0.75 g/mL. This shows that the product had high bulk density.

Embodiment 5

The present invention discloses a method for preparing a new crystalline form of γ-aminobutyric acid, including the steps of:

S1: 100 g crude γ-aminobutyric acid was added to 100 mL water to prepare a γ-aminobutyric acid solution with an initial concentration of 1 g/mL; 0.2 g sodium acetate and 0.2 g potassium acetate were added to the solution, and the temperature was elevated to 60° C.; the mixture was stirred to give a clear solution.

S2: The product of S1 was evaporated under reduced pressure at a temperature of 60° C. and a vacuum of 0.08 MPa for 2.5 hours; 60 mL water was evaporated out, and a suspension was obtained. The suspension was filtered to obtain a wet product, the wet product was dried at 50° C. and atmospheric pressure for 10 hours until its weight was constant. A new crystalline form of γ-aminobutyric acid was obtained as the product.

The purity of the new crystalline form of γ-aminobutyric acid of the present embodiment was 99.7% as determined by high-performance liquid chromatography (HPLC).

An XRD test of the new crystalline form of γ-aminobutyric acid was performed using a D/max-rA X-ray diffractometer from Rigaku Cooperation (Japan). The results showed that the X-ray powder diffraction pattern of the product had characteristic absorption peaks at diffraction angles 2θ of 14.80°, 15.69°, 17.80°, 18.81°, 21.04°, 23.42°, 27.48°, 30.10°, 31.22°, 32.21°, 33.30°, 33.92°, 35.53°, and 38.28°.

DSC (Differential Scanning calorimetry) analysis was used to test the new crystalline form of γ-aminobutyric acid of the present embodiment. The results showed that the product exhibited an endothermic characteristic peak at 222° C.

The new crystalline form of γ-aminobutyric acid of the present embodiment was characterized by Scanning Electron Microscopy (SEM). SEM images showed that the product appeared conical-block-shaped. Its main particle size was 170 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 37°, indicating that the product had good flowability.

The bulk density of the new crystalline form of γ-aminobutyric acid was 0.7 g/mL. This shows that the product had high bulk density.

Embodiment 6

The present invention discloses a method for preparing a new crystalline form of γ-aminobutyric acid, including the steps of:

S1: 90 g crude γ-aminobutyric acid was added to 100 mL water to prepare a γ-aminobutyric acid solution with an initial concentration of 0.9 g/mL; 0.3 g potassium acetate and 0.1 g ammonium acetate were added to the solution, and the temperature was elevated to 70° C.; the mixture was stirred to give a clear solution.

S2: The product of S1 was evaporated under reduced pressure at a temperature of 70° C. and a vacuum of 0.07 MPa for 1.5 hours; 50 mL water was evaporated out, and a suspension was obtained. The suspension was filtered to obtain a wet product, the wet product was dried at 40° C. and atmospheric pressure for 12 hours until its weight was constant. A new crystalline form of γ-aminobutyric acid was obtained as the product.

The purity of the new crystalline form of γ-aminobutyric acid of the present embodiment was 99.4% as determined by high-performance liquid chromatography (HPLC).

An XRD test of the new crystalline form of γ-aminobutyric acid was performed using a D/max-rA X-ray diffractometer from Rigaku Cooperation (Japan). The results showed that the X-ray powder diffraction pattern of the product had characteristic absorption peaks at diffraction angles 2θ of 15.02°, 15.61°, 17.62°, 19.03°, 21.07°, 23.49°, 27.60°, 29.92°, 31.28°, 32.22°, 33.10°, 34.0°, 35.63°, and 38.50°.

DSC (Differential Scanning calorimetry) analysis was used to test the new crystalline form of γ-aminobutyric acid of the present embodiment. The results showed that the product exhibited an endothermic characteristic peak at 220° C.

The new crystalline form of γ-aminobutyric acid of the present embodiment was characterized by Scanning Electron Microscopy (SEM). SEM images showed that the product appeared conical-block-shaped. Its main particle size was 155 μm, its particle size distribution was uniform, and it was not susceptible to absorbing moisture and agglomeration.

The new crystalline form of γ-aminobutyric acid of the present embodiment was slightly ground and smeared on a horizontal background quartz plate, and the angle of repose of the product was measured using a 1050/70 type goniometer. It is generally believed that the smaller the angle of repose, the better the flowability. When the angle of repose is smaller than 40°, flowability requirements in the production process can be met. The measurement result showed that the angle of repose of the new crystalline form of γ-aminobutyric acid obtained was 35°, indicating that the product had good flowability.

The bulk density of the new crystalline form of γ-aminobutyric acid was 0.8 g/mL. This shows that the product had high bulk density.

The purity of the new crystalline form of γ-aminobutyric acid of the present embodiment was above 99%, as determined by high-performance liquid chromatography (HPLC). The crystalline form of the product appeared conical-block-shaped. The main particle size of the product is around 150 μm, and the product has uniform particle size distribution. Comparing to common γ-aminobutyric acids, which have sheet-shaped or needle-shaped crystalline forms, the product of the present embodiment has better bulk density and flowability.

Figure 4:
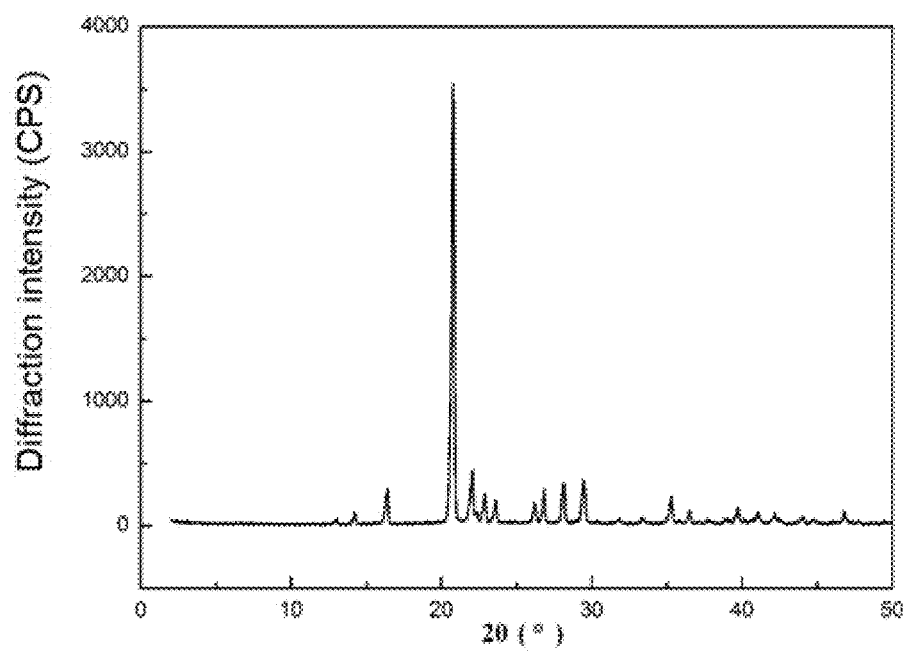
FIG. 4 is an X-ray powder diffraction pattern of a crystalline form of γ-aminobutyric acid of the prior art.

As shown in FIG. 4, the X-ray powder diffraction pattern of a crystalline form of γ-aminobutyric acid of the prior art (patents CN101928736A, CN103509831A, CN104531795A and CN102242161A) had characteristic absorption peaks at diffraction angles 2θ of 13.1°±0.2°, 14.2°±0.2°, 16.4°±0.2°, 21.0°±0.2°, 22.1°±0.2°, 22.9°±0.2°, 23.5°±0.2°, 26.2°±0.2°, 26.8°±0.2°, 28.1°±0.2°, 29.5°±0.2°, 31.8°±0.2°, 33.3°±0.2°, 36.5°±0.2°, and 39.7°±0.2°.

Figure 5:
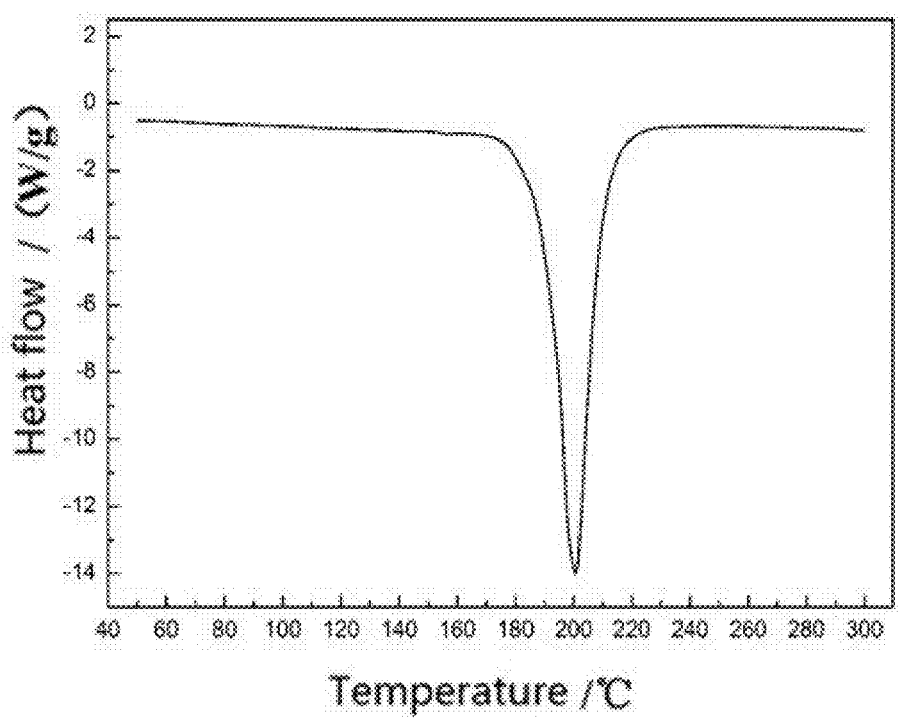
FIG. 5 is a DSC diagram of a crystalline form of γ-aminobutyric acid of the prior art.

As shown in FIG. 5, according to DSC (Differential Scanning calorimetry) analysis, the γ-aminobutyric acid crystal exhibited an endothermic characteristic peak at (201±2) ° C.

The new crystalline form of γ-aminobutyric acid of the present invention is compared with the crystalline form of γ-aminobutyric acid disclosed in patents CN101928736A, CN103509831A, CN104531795A, and CN102242161A. Significant differences have been observed in characteristic absorption peaks of the X-ray powder diffraction pattern, at diffraction angles 2θ of 14.8°±0.2°, 15.7°±0.2°, 17.6°±0.2°, 18.9°±0.2°, 27.5°±0.2°, 29.9°±0.2°, 31.4°±0.2°, 32.2°±0.2°, 33.8°±0.2°, 35.6°±0.2°, and 38.3°±0.2°. In the present invention, the crystalline form and crystal habit of the γ-aminobutyric acid crystal were altered by using a small amount of additive(s) and evaporating and crystallizing under reduced pressure during the crystallization process. A new crystalline form of γ-aminobutyric acid was obtained; it exhibits an endothermic characteristic peak at (220±2) ° C. in DSC analysis, which is approximately 20° C. higher than that of the prior art. This indicates that the product of the present invention has better stability. The new crystalline form of γ-aminobutyric acid of the present invention appeared conical-block-shaped; it has larger crystal size, which significantly increases the bulk density and flowability of the product. The new crystalline form of γ-aminobutyric acid of the present invention could more suitably act as a novel food additive for packaging, storage and use.

The properties of the new crystalline form of γ-aminobutyric acid of the present invention and the crystalline form of γ-aminobutyric acid of the prior art (patents CN101928736A, CN103509831A, CN104531795A, CN102242161A) are shown in the following table:

| Properties | Crystalline forms of γ-aminobutyric acid | |
| --- | --- | --- |
| | CN101928736A, CN103509831A, CN104531795A, CN102242161A | Present invention |
| Crystal habit | Needle-shaped, sheet-shaped | Conical-block-shaped |
| Main particle size | <50 μm | Approx. 150 μm |
| Bulk density | 0.65 g/mL | 0.80 g/mL |
| Angle of repose (flow ability) | 50° | 35° |
| Agglomeration | Serious agglomeration | No agglomeration |
| DSC endothermic characteristic peak | 201° C. | 220° C. |

Comparing with the prior art, the beneficial effects of the new crystalline form of γ-aminobutyric acid and preparation method thereof of the present invention are as follows:

(1) The new crystalline form of γ-aminobutyric acid of the present invention is not susceptible to absorbing moisture and agglomeration, and is convenient for further processing and use.

(2) The new crystalline form of γ-aminobutyric acid of the present invention has large main particle size, uniform particle size distribution, high bulk density, good flowability, and can be easily absorbed and used.

(3) The preparation method of the new crystalline form of γ-aminobutyric acid according to the present invention is simple, easy to operate, low in energy consumption, economical and environmentally friendly. It is suitable for large-scale industrial production.

What is claimed is:

1. A new crystalline form of γ-aminobutyric acid, characterized in that the X-ray powder diffraction pattern of the new crystalline form has characteristic absorption peaks at diffraction angles 2θ of 14.8°±0.2°, 15.7°±0.2°, 17.6°±0.2°, 18.9°±0.2°, 21.0°±0.2°, 23.5°±0.2°, 27.5°±0.2°, 29.9°±0.2°, 31.4°±0.2°, 32.2°±0.2°, 33.3°±0.2°, 33.8°±0.2°, 35.6°±0.2°, 38.3°±0.2°.

2. The new crystalline form of γ-aminobutyric acid according to claim 1, characterized in that the new crystalline form exhibits an endothermic characteristic peak at (220±2) ° C. in DSC analysis.

3. A method for preparing the new crystalline form of γ-aminobutyric acid according to claim 1, characterized in that it includes the steps of:
S1: preparing a γ-aminobutyric acid solution at an initial concentration of 0.5-1.0 g/mL by adding crude γ-aminobutyric acid to water; adding an additive to the γ-aminobutyric acid solution, raising the temperature to 50-80° C., stirring the γ-aminobutyric acid solution to dissolve the solid substances in the solution; and
S2: obtaining a suspension by evaporating water from the product of S1 under reduced pressure and at 50-80° C.; obtaining a wet product by filtering the suspension; drying the wet product to obtain the new crystalline form of γ-aminobutyric acid;
wherein the additive in step S1 is one or more selected from sodium acetate, potassium acetate, and ammonium acetate; the mass ratio of the additive to the crude γ-aminobutyric acid is 0.1:100-0.5:100.

4. The method for preparing a new crystalline form of γ-aminobutyric acid according to claim 3, characterized in that evaporating water under reduced pressure in step S2 is performed under a vacuum of 0.06-0.09 MPa.

5. The method for preparing a new crystalline form of γ-aminobutyric acid according to claim 4, characterized in that in step S2, the volumetric ratio of water evaporated under reduced pressure to water present initially is 30:100 to 80:100, and evaporation time is 0.5 to 4 hours.

6. The method for preparing a new crystalline form of γ-aminobutyric acid according to claim 5, characterized in that the drying in step S2 refers to drying at a temperature of 30-60° C. and under atmospheric pressure for 8-12 hours.

* * * * *